United States Patent [19]

Whittam

[11] 4,397,825

[45] Aug. 9, 1983

[54] ZEOLITES NU-6(1) AND NU-6(2)

[75] Inventor: Thomas V. Whittam, Wilton, England

[73] Assignee: Imperial Chemical Industries PLC, London, England

[21] Appl. No.: 326,026

[22] Filed: Nov. 30, 1981

[30] Foreign Application Priority Data

Dec. 11, 1980 [GB] United Kingdom ............... 8039685

[51] Int. Cl.$^3$ ..................... C01B 33/20; C01B 33/28
[52] U.S. Cl. .................................. 423/277; 252/432; 252/454; 252/455 Z; 423/326; 423/328; 423/329
[58] Field of Search ........................ 423/277, 426–330; 252/431 N, 455 Z; 260/448 C; 546/2, 13, 14

[56] References Cited

U.S. PATENT DOCUMENTS

| | | | |
|---|---|---|---|
| 3,436,174 | 4/1969 | Sand | 423/328 |
| 3,720,753 | 3/1973 | Robson | 423/328 |
| 3,760,062 | 9/1973 | Sand et al. | 423/328 |
| 4,211,760 | 7/1980 | Grose et al. | 423/328 |

Primary Examiner—Edward J. Meros
Attorney, Agent, or Firm—Cushman, Darby & Cushman

[57] ABSTRACT

New zeolite materials designated Nu-6(1) and Nu-6(2), having molar compositions expressed by the formula:

0.5 to 1.5 $R_2O:Y_2O_3$:at least 10 $XO_2$:0 to 2000 $H_2O$ wherein R is a monovalent cation or $1/n$ of a cation of valency n, X is silicon, and/or germanium, Y is one or more of aluminum, iron, chromium, vanadium, molybdenum, antimony, arsenic, manganese, gallium or boron, and $H_2O$ is water of hydration additional to water notionally present when R is H and having defined X-ray diffraction patterns, are prepared from a reaction mixture containing $XO_2$ (preferably silica), $Y_2O_3$ (preferably alumina) and a 4,4'-bipyridyl compound. At temperatures of 200° C. or higher, Nu-6(1) is converted to Nu-6(2), a useful catalyst for xylenes isomerization and the like.

23 Claims, No Drawings

ZEOLITES NU-6(1) AND NU-6(2)

The present invention relates to novel zeolite materials hereinafter referred to as zeolites Nu-6(1) and Nu-6(2), to a method of making them and to processes using Nu-6(2) as a catalyst.

According to the present invention we provide zeolites Nu-6(1) and Nu-6(2) having molar compositions expressed by the following formula:

0.5 to 1.5 $R_2O:Y_2O_3$: at least 10 $XO_2$:0 to 2000 $H_2O$ wherein R is a monovalent cation or 1/n of a cation of valency n, X is silicon, and/or germanium, Y is one or more of aluminium, iron, chromium, vanadium, molybdenum, antimony, arsenic, manganese, gallium or boron, and $H_2O$ is water of hydration additional to water notionally present when R is H, and having X-ray diffraction patterns substantially as set out in Tables 1 and 2 (as determined by standard technique using copper K $\alpha$ radiation). Table 1 shows X-ray data for zeolite Nu-6 (1) as prepared.

wherein M is an alkali metal and/or ammonium and can include hydrogen, and $M_2O+Q$ is equal to or greater than 1.0.

Typically, the Nu-6(1), structure retains from 0.01 to 0.15 moles of Q per mole of $XO_2$, Q in this case being a 4,4'-bipyridyl compound.

The $H_2O$ content of freshly prepared zeolite Nu-6(1) depends on the conditions in which it has been dried after synthesis. Indeed, if dried at temperatures at or above 200° C. it converts to zeolite Nu-6(2).

In calcined forms of zeolite Nu-6(2), R may be alkali metal but includes less or no nitrogen-containing organic compounds, since these are burnt out in the presence of air leaving hydrogen as the other balancing cation, or otherwise displaced prior to calcination.

The above mentioned behaviour of zeolite Nu-6(1) on heating makes it unique in high silica zeolites. Thus, when as-made Nu-6(1) is heated at temperatures of from 200° to 750° C., it recrystallises to a novel crystalline phase designated zeolite Nu-6(2). Zeolite Nu-6(1) as made crystallises as thin plates, typically having dimensions in the range from $1\mu \times 2\mu \times 0.1\mu$ to $10\mu \times 30\mu \times 1\mu$. On recrystallisation to Nu-6(2), the

TABLE 1

| | | | | | | | ZEOLITE Nu-6(1) | | | | | | | | | | | |
|---|---|---|---|---|---|---|---|---|---|---|---|---|---|---|---|---|---|---|
| dA | 13.4 | 11.3 | 6.89 | 5.46 | 4.52 | 4.48 | 4.29 | 4.23 | 3.998 | 3.683 | 3.478 | 3.382 | 3.335 | 3.107 | 3.109 | 2.986 | 2.964 | 2.484 |
| 100$I/I_o$ | 89 | 6 | 3 | 13 | 17 | 15 | 84 | 19 | 100 | 34 | 40 | 91 | 61 | 13 | 11 | 3 | 3 | 17 |

Within the above definition of chemical composition, the number of moles of $XO_2$ is typically in the range 10 to 5000 and zeolites Nu-6(1) and Nu-6(2) appear to be most readily formed in a state of high purity when the number of moles of $XO_2$ is in the range 20 to 1000.

This definition includes both freshly prepared Nu-6(1) and Nu-6(2) ("freshly prepared" means the product of synthesis and washing, with optional drying, as hereinafter described) and also forms resulting from dehydration, and/or calcination, and/or ion exchange. In freshly prepared Nu-6(1) and Nu-6(2), R may include an alkali metal cation, especially sodium, and/or ammonium, and hydrogen, and usually includes nitrogen-containing organic cations as described below. These nitrogen-containing cations are hereinafter referred to as Q.

The freshly prepared Nu-6(1) and Nu-6(2) may also contain nitrogen-containing compounds well in excess of the 1.5 moles set out in the aforesaid definition of the composition of Nu-6(1) and Nu-6(2), typically in the range 0.1 to 20 moles per mole of $Y_2O_3$. Since Nu-6(1) and Nu-6(2) are zeolites, the nitrogen-containing base must be physically trapped within the crystal lattice. It can be removed by thermal or oxidative degradation or by displacement by suitable small molecules. This physically trapped basic material does not constitute part of the composition for the purpose of the definition. Thus Nu-6(1) or Nu-6(2) as made typically has the following molar composition:

0 to 1.8 $M_2O$:1.0 to 400 Q:$Y_2O_3$:10 to 5000 $XO_2$:0 to 2000 $H_2O$ plates remain intact. However, X-ray results suggest these plates are now agglomerates of much smaller crystals. Table 2 gives typical X-ray diffraction data for zeolite Nu-6(2).

All diffraction lines show some broadening, those marked B are the broadest. Significant line broadening appears to be a characteristic of zeolite Nu-6(2). The degree of broadening depends upon the temperature. The effect of temperature on line broadenings is shown in Table 3 for the diffraction peaks at d-spacings 8.41, 6.67 and 3.33. No significant changes occur from 450° to 750° C. At 800° C. sodium Nu-6(2) as made in Example 2 recrystallised to $\alpha$-crystobalite.

TABLE 2

| | | | | | ZEOLITE Nu-6(2) | | | | | | | |
|---|---|---|---|---|---|---|---|---|---|---|---|---|
| dA | 8.41 | 6.67 | 6.09 | 4.61 | 4.33 | ca 4.19 | ca 4.10 | 3.94 | 3.76 | 3.65 | 3.44 | 3.33 | 3.17 | 3.05 |
| 100$I/I_o$ | 45 B | 42 | 15 B | 27.5 | 100 | shoulder | | 2 B | 11 B | 15 B | 27 B | 76 | 15 B | 9 |

TABLE 3

| | ZEOLITE Nu-6(2) | | |
|---|---|---|---|
| Temperature of treatment °C. | Line breadth Bo (2θ) at ½ peak height | | |
| | d-spacing 8.41A | d-spacing 6.67A | d-spacing 3.33A |
| 300 | 1.4 | 0.3 | 0.6 |
| 350 | 1.3 | 0.28 | 0.55 |
| 400 | 1.2 | 0.29 | 0.5 |
| 450 | 0.4 | 0.28 | 0.4 |

As recrystallisation occurs there is no indication from X-ray evidence of lattice shrinkage in Nu-6(1). The latter merely disappears and is replaced by Nu-6(2). Thus, at temperatures below 450° C. the conversion is relatively slow, e.g. at 250° C. complete conversion requires 72 hours. During the intermediate stages of this recrystallisation X-ray evidence shows that both Nu- 6(1) and Nu-6(2) coexist, and Nu-6(1) disappears only when most of the organic component has been removed. At 450° C. and higher, the conversion from Nu-6(1) to Nu-6(2) is very rapid. Typical sorption data for zeolite Nu-6(2) of Example 8 are given in Table 4.

TABLE 4

| Sorbate | SORPTION AT 25° C., p/po = 0.5, 2 hours | | | | |
|---|---|---|---|---|---|
| | n-hexane | p-xylene | m-xylene | cyclohexane | water* |
| sorption % w/w | 8.0 | 7.3 | 5.9 | 4.8 | 3.9 |

*at p/po = 0.25

These results suggest that zeolite Nu-6(2) has entrance ports of around 6.5 A, and also shows marked hydrophobic behaviour.

This invention provides also a method of making zeolites Nu-6(1) and Nu-6(2) which comprises reacting an aqueous mixture containing at least one oxide $XO_2$, at least one oxide $Y_2O_3$ and a 4,4'-bipyridyl compound.

The reaction mixture preferably has the following molar composition:

| | | |
|---|---|---|
| $XO_2/Y_2O_3$ | 10 to 5000 | preferably 20 to 3000 |
| $MOH/XO_2$ | 0 to 1.0 | preferably 0.01 to 0.3 |
| $Z^{31}/Y_2O_3$ | 10 to 5000 | preferably 10 to 100 |
| $Q/Y_2O_3$ | 0.1 to 5000 | preferably 1 to 500 |
| $H_2O/XO_2$ | 10 to 500 | preferably 15 to 300 |
| $BOH/Y_2O_3$ | 0 to 500,000 | preferably 0 to 1000 | where X is silicon and/or germanium, Y is one or more of aluminum, gallium, iron, chromium, vanadium, molybdenum, antimony, arsenic, manganese or boron, M is an alkali metal or ammonium, Q is the aforesaid 4,4'-bipyridyl compound and Z− is a strong acid radical present as a salt of M and may be added as a free acid to reduce the free OH− level to a desired value. M and/or Q can be present as hydroxides or salts or inorganic or organic acids provided the $MOH/XO_2$ requirement is fulfilled. BOH is an aliphatic or aromatic alcohol, preferably an alkanol. Whilst not essential, an alcohol improves crystallisation in viscous reaction mixtures.

The bipyridyl may be partially or fully alkylated, e.g. methylated.

The preferred bipyridyl compound is 4,4'-bipyridyl itself.

The preferred alcohol (BOH) is methanol.

The preferred alkali metals (M) are sodium and potassium. The preferred oxide $XO_2$ is silica ($SiO_2$) and the preferred oxide $Y_2O_3$ is alumina ($Al_2O_3$).

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fume silicas and silica gels suitably in grades for use in reinforcing pigments for rubber or silicone rubber. Colloidal silicas of various particle sizes may be used, for example 10-15 or 40-50 microns, as sold under the Registered Trade Marks "LUDOX," "NALCOAG" and "SYTON." The usable dissolved silicas include commercially available water glass silicates containing 0.5 to 6.0, especially 2.0 to 4.0 mols of $SiO_2$ per mole of alkali metal oxide, "active" alkali metal silicates as defined in U.K. Pat. No. 1,193,254, and silicates made by dissolving silica in an alkali metal hydroxide or quaternary ammonium hydroxide or a mixture thereof.

The alumina source is most conveniently sodium aluminate, but can be or can include aluminum, an aluminum salt of example the chloride, nitrate or sulphate, an aluminium alkoxide or alumina itself, which should preferably be in a hydrated or hydratable form such as colloidal alumina, pseudoboehmite, boehmite, gamma alumina or the alpha or beta trihydrate.

The reaction mixture is reacted usually under autogenous pressure, optionally with added gas, e.g. nitrogen at a temperature between 85° and 250° C. until crystals of Nu-6(1) and/or Nu-6(2) form, which can be from 1 hour to many months depending on the reactant composition and the operating temperature. Agitation is optional, but is preferable since it reduces the reaction time.

At the end of the reaction, the solid phase is collected on a filter and washed and is then ready for further steps such as drying, dehydration and ion-exchange.

If the product of the reaction contains alkali metal ions, these have to be at least partly removed in order to prepare more acid forms of Nu-6(2) and this can be done by ion exchange with an acid, especially a strong mineral acid such as hydrochloric acid or by way of the ammonium compound, made by ion exchange with a solution of an ammonium salt such as ammonium chloride. Such ion exchange can be carried out by slurrying once or several times with the solution.

In general, the cation(s) of zeolite Nu-6(1) and Nu-6(2) can be replaced by any cation(s) of metals, and particularly those in Groups IA, IB, IIA, IIB, III (including rare earths) VIII (including noble metals) and by lead, tin and bismuth. (The Periodic Table is as in "Abridgements of Specifications" published by the U.K. patent Office). Exchange is carried out using any water soluble salts containing the appropriate cation.

In order to prepare a catalyst, zeolite Nu-6(1) or Nu-6(2) may be used in association with an inorganic matrix, or with other materials which can be either inert or catalytically active. The matrix may be present simply as a binding agent to hold the small zeolite particles (0.005 to 10 microns) together, or it may be added as a diluent to control the amount of conversion in a process which may otherwise proceed at too high a rate, leading to catalyst fouling as a result of excessive coke formation. Typical inorganic diluents include catalyst support materials such as alumina, silica, kaolinic clays, bentonites, montmorillonites, sepiolite, attapulgite, Fullers earth, synthetic porous materials such as $SiO_2$-$Al_2O_3$, $SiO_2$-$ZrO_2$, $SiO_2$-$ThO_2$, $SiO_2$-$BeO$, $SiO_2$-$TiO_2$ or any combination of these oxides. An effective way of mixing zeolites Nu-6(1) or Nu-6(2) with such diluents is to mix appropriate aqueous slurries in a mixing nozzle and then to spray-dry the slurry. Other ways of mixing can be used.

If zeolite Nu-6(1) or Nu-6(2) in any cationic form or as a catalytic composite is exchanged or impregnated with hydrogenation/dehydrogenation components, such as Ni, Co, Pt, Pd, Re, Rh, hydrocracking and reforming catalysts can be made, especially if the $Na_2O$ content is less than 0.1% w/w.

A wide range of hydrocarbon conversion catalysts can be prepared from zeolite Nu-6(1) or Nu-6(2) by ion exchange or impregnation with cations, or oxides, selected from the following, Cu, Ag, Mg, Ca, Sr, Zn, Cd, B, Al, Sn, Pb, V, P, Sb, Cr, Mo, W, Mn, Re, Fe, Co, Ni noble metals, Usually the Nu-6(2) catalyst will be in acid form, thus stoichiometry is maintained by $H^+$ or $H_3O^+$ as an additional balancing cation, or as sole cation. Such catalysts may find application in the following processes; catalytic cracking, hydrodesulphurization, hydrodenitrification, catalytic dewaxing, alkylation of alkanes or aromatics, dealkylation, disproportionation, isomerisation of alkanes and alkyl benzenes, dehydration reactions, oxidation and polymerisation.

We have found that zeolite Nu-6(2) is especially useful as a catalyst for xylenes isomerisation. As is well known, the major aim in xylenes isomerisation is to increase the para-xylenes content of the feedstock at the expense of other isomers since para-xylene is a particularly useful and valuable product. The mixed xylenes feedstocks commonly available for xylenes isomerisation usually contain amounts of the three xylene isomers as well as ethylbenzene. Hitherto, some of the mixed xylenes feedstock available has contained relatively small amounts of ethylbenzene but it is anticipated that in the furture such feedstocks will become more expensive and that resort will have to be made to feedstocks containing rather larger amounts of ethylbenzene, say up to about 25% ethylbenzene.

In our copending U.K. application No. 8,039,686 there is disclosed the use of Nu-6(2) as a superior xylenes isomerisation catalyst.

Zeolite Nu-6(2) may also find applications in pollution control by its ability to remove organic contaminants from aqueous effluents.

The invention is illustrated by the following Examples.

EXAMPLE 1

Preparation of sodium 4,4'-bipyridyl Nu-6(1). The synthesis mixture had the following molar composition:
23.9 $Na_2O$, 12.7 Q, $Al_2O_3$, 90 $SiO_2$, 2996 $H_2O$, 237 EtOH,
19.5 $SO_4^{2-}$ where Q is 4,4'-bipyridyl.
(a) 24.8 g 4,4'-bipyridyl were dissolved in 136 g ethanol to give solution A;
(b) 215 g Q-79 ($Na_2O$, 0.01 $Al_2O_3$, 3.77 $SiO_2$, 24 $H_2O$) were diluted with 200 g water to give solution B;
(c) 6 g aluminum sulphate ($Al_2O_3$, 3 $SO_3$, 16 $H_2O$) and 21.5 g 98% sulphuric acid were dissolved in 342 g water to give solution C.

Next solution B was stirred into solution A followed by solution C. The mixture was reacted in a stirred stainless steel autoclave for 3 days at 140° C. After cooling to about 60° C., the slurry was filtered and washed with 2 liters of distilled water at about 60° C., and dried overnight at 120° C. The product was sodium 4,4'-bipyridyl Nu-6 i.e. Nu-6(1) and had X-ray data as shown in Table 1, and a molar composition:
1.52 $Na_2O$, 5Q, $Al_2O_3$, 65 $SiO_2$, 14.5 $H_2O$

EXAMPLE 2

Part of the product of Example 1 was calcined in moist air at 450° C. for 48 hours. The product was sodium hydrogen Nu-6(2) with X-ray data as shown in Table 2.

EXAMPLE 3

Part of the product of Example 2 was slurried with 4 ml of 2 N hydrochloric acid per g at 90° C. for 1 hour. The product of acid exchange was washed with 10 ml water per g of zeolite dried overnight at 120° C. and activated for sorption by calcining in air at 450° C. for 6 hours. The X-ray data for this product was again as shown in Table 2 and its molar composition was:
0.25 $Na_2O$, $Al_2O_3$, 74.6 $SiO_2$ Therefore although a substantial level of sodium was removed by ion exchange, this result suggests that 25% of the cation basis sites in this sample of sodium hydrogen Nu-6(2) were filled by sodium. Surprisingly, this product was a very active acidic catalyst in xylene isomerisation reactions.

EXAMPLE 4

The reaction of Example 1 was repeated except that no ethanol was added. The product after 3 and 5 days at 140° C. was amorphous.

EXAMPLE 5

The reaction of Example 1 was scaled down by a factor of two and was carreid out in a stirred pyrex (RTM) reactor under reflux at 105° C. The product after 20 days was identical with that of Example 1.

EXAMPLE 6

The synthesis mixture had the following molar composition and contained no ethanol:
18.6 $Na_2O$, 10.8 Q, $Al_2O_3$, 70 $SiO_2$, 2433 $H_2O$, 16.9 $H_2SO_4$
(a) 20.6 g Q-79 were diluted with 2.47 g water, and 26 g 4,4'-bipyridyl were added with stirring (Slurry A)
(b) 7.9 g aluminum sulphate and 21.8 g 98% sulphuric acid were dissolved in 300 g water (Solution B)

Solution B was stirred into Slurry A and the mixture was reacted in a stainless steel stirred autoclave for 5 days at 140° C. The product was filtered, washed and dried as in Example 1, and had X-ray diffraction data as shown in Table 5 and was an excellent sample of zeolite Nu-6(1).

EXAMPLE 7

The synthesis mixture had the following molar composition:
79.6 $Na_2O$, 46.2 Q, $Al_2O_3$, 300 $SiO_2$, 1042 $H_2O$, 75.2 $SO_4$
(a) 191.3 g Q-79 were diluted with 210.6 g water, and 24 g 4,4'-bipyridyl were added with stirring to give (Slurry A)
(b) 0.4 g aluminum sulphate and 24.5 g 98% solphuric acid were stirred into 300 g water (Solution B).

Solution B was stirred into Slurry A and the mixture was reacted for 3 days at 140° C. The product was filtered, washed and dried as in Example 1, and had the X-ray diffraction data given in Table 6, and was a highly crystalline sample of zeolite Nu-6(1). The molar composition of this as-made sample of Nu-6(1) was:
1.3 $Na_2O$, 31 Q, $Al_2O_3$, 230 $SiO_2$, 54 $H_2O$ This sample was calcined at 450° C. for 72 hours in a flowing, humid air-stream. The resulting zeolite Nu-6(2) had the X-ray data as shown in Table 7.

EXAMPLE 8

The product of Example 7 was slurried with 4 ml of 2 N hydrochloric acid per g at 90° C. for 1 hours. After filtration and washing the acid treatment was repeated. The final product was washed with 20 ml of water per g of zeolite, dried overnight at 105° C. and finally calcined in moist air at 450° C. for 6 hours. This product was used in the sorption experiments of Table 4 and it had the following molar composition:
0.2 Na$_2$O, Al$_2$O$_3$, 246 SiO$_2$

EXAMPLE 9

In this example the synthesis mixture had the following molar composition:
9 Na$_2$O, 7.4Q, Al$_2$O$_3$, 90 SiO$_2$, 1500 H$_2$O
(a) 411 g Syton X-30 (Na$_2$O, 0.04 Al$_2$O$_3$, 85.6 SiO$_2$ 689 H$_2$O) were diluted with 280 g water and 24 g 4,4'-bipyridyl were added with stirring to give (Slurry A)

which had the following molar composition after drying at 105° C. for 7 hours. 1.3 Na$_2$O, 80 Q, Al$_2$O$_3$, 2000 SiO$_2$, 300 H$_2$O. The product had the X-ray data given in Table 9.

On calcination at 450° C. for 72 hours, the usual transformation to zeolite Nu-6(2) occurred as shown by X-ray data given in Table 10.

EXAMPLE 11

The synthesis mixture had the following molar composition:
18.5 Na$_2$O, 10.8 Q, Al$_2$O$_3$, 70 SiO$_2$, 2420 H$_2$O, 12.1

TABLE 5

| dA | 13.4 | 9.1 | 6.8 | 5.51 | 4.67 | 4.50 | 4.29 | 4.00 | 3.693 | 3.480 | 3.395 | 3.339 | 3.089 | 2.788 | 2.648 | 2.485 |
|---|---|---|---|---|---|---|---|---|---|---|---|---|---|---|---|---|
| 100$^I$/Io | 100 | 16 | 16 | 13 | 16 | 20 | 76 | 93 | 27 | 46 | 88 | 58 | 16 | 13 | 9 | 13 |

TABLE 6

| dA | 13.4 | 6.73 | 5.47 | 4.67 | 4.47 | 4.28 | 3.995 | 3.693 | 3.486 | 3.382 | 3.339 | 3.110 | 3.079 | 2.618 | 2.485 | 2.243 | 2.000 | 1.894 | 1.841 |
|---|---|---|---|---|---|---|---|---|---|---|---|---|---|---|---|---|---|---|---|
| 100$^I$/Io | 67 | 11 | 14 | 4 | 19 | 89 | 100 | 31 | 32 | 99 | 49 | 18 | 8 | 6 | 18 | 7 | 9 | 5 | 4 |

TABLE 7

| dA | 8.38 | 6.65 | 6.07 | 4.631 | 4.266 | 4.064 | 3.931 | 3.764 | 3.424 | 3.329 | 3.176 | 3.039 |
|---|---|---|---|---|---|---|---|---|---|---|---|---|
| 100$^I$/Io | 40 | 33 | 13 | 33 | 100 | 18 | 9 | 17 | 25 | 71 | 14 | 7 |
| dA | 2.807 | 2.634 | 2.503 | 2.473 | 2.418 | 2.339 | 2.145 | 2.078 | 2.021 | 1.937 | 1.851 | |
| 100$^I$/Io | 6 | 5 | 10 | 7 | 7 | 6 | 2 | 7 | 14 | 2 | 2 | |

(b) 5 g sodium aluminate (1.25 Na$_2$O, Al$_2$O$_3$ 3H$_2$O) were dissolved in 26.5 g water (Solution B).

Solution B was stirred into Slurry A and the mixture was reacted for 3 days at 140° C. The product was filtered, washed and dried as in Example 1 and had the X-ray diffraction data given in Table 8.

SO$_4^{2-}$
The reaction was exactly as Example 7 except that the weights of reactants were as follows: 206 g Q-79, 247 g water, 26 g 4,4'-bipyridyl, 7.9 g aluminum sulphate, 14.9 g sulphuric acid and 300 g water.

The Nu-6(1) product had the following molar com-

TABLE 8

| dA | 13.4 | 9.03 | 6.94 | 6.73 | 6.56 | 6.37 | 6.03 | 5.75 | 5.46 | 4.67 | 4.51 | 4.29 |
|---|---|---|---|---|---|---|---|---|---|---|---|---|
| 100$^I$/Io | 86 | 16 | 4 | 13 | 18 | 5 | 3 | 8 | 13 | 4 | 34 | 76 |
| dA | 4.10 | 3.995 | 3.678 | 3.480 | 3.382 | 3.339 | 3.215 | 3.105 | 2.885 | 2.618 | 2.478 | 2.002 |
| 100$^I$/Io | 18 | 100 | 21 | 44 | 86 | 43 | 17 | 10 | 7 | 4 | 15 | 5 |

The molar composition of the as-made Nu-6(1) product was 1.6 Na$_2$O, 3Q, Al$_2$O$_3$, 50 SiO$_2$, 13.5 H$_2$O.

EXAMPLE 10

This Example illustrates the preparation of highly siliceous Nu-6(1) and Nu-6(2). The synthesis mixture had the following molar composition: 31.4 Na$_2$O, 325 Q, Al$_2$O$_3$, 2167 SiO$_2$, 36189 H$_2$O 39 g of 4,4'-bipyridyl were dissolved at 60° C. in 260 g water containing 0.4 g sodium hydroxide. This solution was stirred into 343 g of colloidal silica (Syton X-30) also at 60° C. The mix was homogenised at 60° C. for 30 minutes and then transferred to a 1 liter, stirred, stainless steel autoclave. The reaction was carried out for 5 days at 180° C. The product was a very pure sample of sodium Nu-6(1), position after drying at 105° C. for 17 hours. 1.1 Na$_2$O, 4.2 Q, Al$_2$O$_3$, 39 SiO$_2$, 10 H$_2$O, and the following X-ray data shown in Table 11.

EXAMPLE 12

The synthesis mixture had the following molar composition:
9 K$_2$O, 7 Q, Al$_2$O$_3$, 90 SiO$_2$, 1502 H$_2$O.

2.9 g pseudoboehmite (Al$_2$O$_3$, 3 H$_2$O) were dissolved in 47 g water containing 18.7 g potassium hydroxide by boiling for 1 hour under reflux. The resulting solution was cooled to about 25° C. and stirred into a slurry containing 100 g Degussa Aerosil 200, 20.2 g 4,4'-bipyridyl and 449 g water. The mixture was reacted for 6 days at 180° C. in a stirred stainless steel autoclave.

TABLE 9

| dA | 13.4 | 6.93 | 6.74 | 5.49 | 4.650 | 4.491 | 4.286 | 3.994 | 3.687 | 3.483 | 3.379 | 3.330 |
|---|---|---|---|---|---|---|---|---|---|---|---|---|
| 100$^I$/Io | 100 | 2 | 14 | 13 | 2 | 23 | 82 | 77 | 25 | 25 | 92 | 49 |
| dA | 3.235 | 3.103 | 2.799 | 2.736 | 2.619 | 2.478 | 2.332 | 2.245 | 2.019 | 2.000 | 1.842 | |
| 100$^I$/Io | 2 | 14 | 3 | 4 | 5 | 12 | 7 | 9 | 10 | 10 | 2 | |

TABLE 10

| dA | 8.25 | 6.62 | 6.04 | 4.589 | 4.237 | 4.139 | 4.037 | 3.740 | 3.418 | 3.329 | 3.145 | 3.030 | 2.896 | 2.623 | 2.594 | 2.480 | 2.460 | 2.414 | 2.337 |
|---|---|---|---|---|---|---|---|---|---|---|---|---|---|---|---|---|---|---|---|
| $100I/Io$ | 100 | 30 | 14 | 46 | 71 | 56 | 22 | 24 | 20 | 99 | 25 | 6 | 2 | 6 | 6 | 9 | 9 | 6 | 4 |

| dA | 2.278 | 2.232 | 2.192 | 2.144 | 2.127 | 2.072 | 2.028 | 2.005 | 1.981 | 1.926 | 1.837 |
|---|---|---|---|---|---|---|---|---|---|---|---|
| $100I/Io$ | 4 | 2 | 2 | 3 | 4 | 1 | 3 | 6 | 4 | 1 | 4 |

TABLE 11

| dA | 13.4 | 9.02 | 6.72 | 6.57 | 6.40 | 6.04 | 5.77 | 5.47 | 4.661 | 4.502 | 4.280 | 3.993 | 3.827 | 3.739 | 3.681 | 3.474 | 3.380 | 3.330 |
|---|---|---|---|---|---|---|---|---|---|---|---|---|---|---|---|---|---|---|
| $100I/Io$ | 70 | 5 | 12 | 6 | 2 | 1 | 3 | 12 | 3 | 20 | 78 | 100 | 3 | 9 | 24 | 42 | 92 | 49 |
| dA | 3.216 | 3.100 | 3.071 | 2.886 | 2.807 | 2.734 | 2.690 | 2.618 | 2.480 | 2.424 | 2.404 | 2.334 | 2.244 | 2.168 | 2.023 | 1.998 | 1.890 | 1.841 |
| $100I/Io$ | 9 | 14 | 10 | 3 | 2 | 4 | 1 | 4 | 17 | 5 | 5 | 7 | 5 | 3 | 8 | 8 | 3 | 4 |

The product was filtered, washed and dried as in previous experiments, and was found to be potassium Nu-6(1) with X-ray data as shown in Table 12.

After calcination for 72 hours at 450° C., the usual transformation to zeolite Nu-6(2) occurred. X-ray data

TABLE 12

| dA | 13.3 | 8.45 | 7.10 | 6.73 | 5.49 | 4.502 | 4.282 | 3.992 | 3.676 | 3.487 | 3.377 | 3.318 | 3.235 | 3.099 | 2.922 | 2.800 | 2.737 | 2.619 |
|---|---|---|---|---|---|---|---|---|---|---|---|---|---|---|---|---|---|---|
| $100I/Io$ | 89 | 3 | 10 | 13 | 14 | 45 | 100 | 97 | 49 | 78 | 92 | 38 | 11 | 19 | 12 | 7 | 8 | 8 |

| dA | 2.477 | 2.424 | 2.244 | 2.165 | 1.078 | 1.994 | 1.925 | 1.889 | 1.839 |
|---|---|---|---|---|---|---|---|---|---|
| $100I/Io$ | 13 | 8 | 9 | 3 | 12 | 9 | 3 | 3 | 1 |

TABLE 13

| dA | 8.32 | 6.66 | 6.09 | 4.607 | 4.29 | 4.158 | 4.060 | 3.753 | 3.429 | 3.325 | 3.159 | 3.047 |
|---|---|---|---|---|---|---|---|---|---|---|---|---|
| $100I/Io$ | 90 | 39 | 18 | 56 | 100 | 63 | 40 | 26 | 22 | 87 | 20 | 4 |
| dA | 2.843 | 2.640 | 2.606 | 2.499 | 2.419 | 2.345 | 2.146 | 2.126 | 2.017 | 1.934 | 1.843 | |
| $100I/Io$ | 2 | 6 | 7 | 11 | 8 | 7 | 4 | 2 | 2 | 1 | 4 | | for potassium hydrogen Nu-6(2) is given in Table 13.

EXAMPLE 13

This Example was as Example 10, except that 3.4 g antimonious oxide were stirred into the mixture before transferring to the autoclave. The dried Nu-6(1) product obtained contained 3% $Sb_2O_3$ but only 0.07% $Al_2O_3$ by weight. On calcination in moist air at 450° C. for 72 hours, the characteristic transformation to Nu-6(2) occurred.

EXAMPLES 14 TO 17

In these Examples as with Example 13, additional compounds were introduced into an Example 10 type reaction. However, in each instance the compound was dissolved in the bipyridyl/alkali solution. In every case the product was Nu-6(1) which transformed to Nu-6(2) on calcination.

In Example 14, the additive was 5.8 g potassium chrome alum. The dried Nu-6(1) contained 0.8% $Cr_2O_3$ and only 0.07% $Al_2O_3$ by weight. In Example 15, the additive was 2.9 g boric acid and the Nu-6(1) product contained 0.8% $B_2O_3$ and 0.07% $Al_2O_3$ by weight.

In Example 16, the additive was 8.5 g sodium vanadate and the Nu-6(1) product contained 0.9% V and only 0.06% $Al_2O_3$ by weight.

In Example 17, the additive was 6.6 g disodium hydrogen phosphate. The dried Nu-6(1) contained 0.6% P and 0.07% $Al_2O_3$ by weight.

EXAMPLE 18

The synthesis mixture had the following molar composition:
3 $Na_2O$, 6Q, $Al_2O_3$, 30 $SiO_2$, 834 $H_2O$.

72 g of Degussa Aerosil 200 were dispersed in a solution containing 12.4 g of 4,4'-bipyridyl and 560 g water at 60° C. Next, 8 g sodium aluminate and 5.8 g sodium hydroxide dissolved in 41 g water at 60° C. were stirred in. The mixture was homogenised for 15 minutes and reacted for 5 days at 180° C. in a stirred stainless steel autoclave. The Nu-6(1) product had the following molar composition after drying for 17 hours at 105° C.:
1.1 $Na_2O$, 2.7 Q, $Al_2O_3$, 24 $SiO_2$, 4.8 $H_2O$.

EXAMPLE 19

This Example illustrates the use of hydrogen ion exchanged Nu-6(2) in toluene disproportionation.

The product from Example 3 was calcined in air at 450° C. for 48 hours, and acid exchanged with N hydrochloric acid. The product was filtered and washed with deionised water, dried overnight at 105° C. and calcined at 450° C. for 16 hours.

Approximately 2 g of the product thus obtained was compressed, crushed and sieved. 0.44 g of 250–500μ particles of HNu-6(2) so prepared were loaded into a microreactor for testing as a toluene disproportionation catalyst. The catalyst was flushed with nitrogen for 2 hours while heating to 528° C. prior to contact with toluene reactant. The reaction temperature was 528° C. and the toluene was fed at a WHSV of 10.9. The results of this reaction are given in Table 14.

It will be evident from Table 14 that after 20 hours on line the activity of the HNu-6(2) sample had only decayed to half of its original value.

TABLE 14

| Time on Stream hrs | Toluene Conversion wt % | wt % p-xylene in xylenes fraction |
|---|---|---|
| 0.1 | 8.0 | 26.2 |
| 10.4 | 6.0 | 26.8 |
| 16.4 | 4.6 | 28.2 |
| 21.9 | 4.0 | 28.7 |

I claim:

1. Zeolite and Nu-6(2) having molar compositions expressed by the following formula:
0.5 to 1.5 $R_2O$: $Y_2O_3$: at least 10 $XO_2$: 0 to 2000 $H_2O$
wherein R is a monovalent cation or 1/n of a cation of valency n, X is silicon, and/or germanium, Y is one or more of aluminum, iron, chromium. vanadium, molybdenum, antimony, arsenic, manganese, gallium or boron, and $H_2O$ is water of hydration additional to water notionally present when R is H, and having X-ray diffraction patterns substantially as set out in Table 2.

2. Zeolite and Nu-6(2) according to claim 1 wherein the molar composition is expressed by the formula:
0.5 to 1.5 $R_2O$: $Y_2O_3$: 20 to 1000 $XO_2$: 0 to 2000 $H_2O$.

3. Zeolite and Nu-6(2) according to claim 1 as freshly made having a molar composition expressed by the formula:
0 to 1.8 $M_2O$: 1.0 to 400 Q: $Y_2O_3$: 10 to 5000 $XO_2$: 0 to 2000 $H_2O$
wherein M is an alkali metal, ammonium or hydrogen, Q is a 4,4'-bipyridyl compound and $M_2O+Q$ is equal to or greater than 1.0.

4. Zeolite Nu-6(2) according to claim 1 or claim 2 wherein R is or includes hydrogen.

5. A method of making zeolite precursor material Nu-6(1) having molar compositions expressed by the following formula 0.5 to 1.5 $R_2O$: $Y_2O_3$: at least 10 $XO_2$: 0 to 2000 $H_2O$ wherein R is a monovalent cation or 1/n of a cation of valency n, x is silicon and/or germanium, Y is one or more of aluminum, iron, chromium, vanadium, molybdenum, antimony, arsenic, manganese, gallium or boron, and $H_2O$ is water of hydration additional to water notionally present when R is H, and having diffraction patterns substantially as set out in Table 1, which method comprises reacting an aqueous mixture containing at least one oxide $XO_2$, at least one oxide $Y_2O_3$ and a 4,4'-bipyridyl compound.

6. A method according to claim 5 wherein the aqueous mixture has the following molar composition:
$XO_2/Y_2O_3$—10 to 5000
$MOH/XO_2$—0 to 1.0
$Z^-/Y_2O_3$—0 to 5000
$Q/Y_2O_3$—0.1 to 5000
$H_2O/XO_2$—10 to 500
$BOH/Y_2O_3$—0 to 500,000
wherein X is silicon and/or germanium, Y is one or more of aluminum, gallium, iron, chromium, vanadium, molybdenum, antimony, arsenic, manganese or boron, M is an alkali metal or ammonium, Q is a 4,4'-bipyridyl compound, $Z^-$ is a strong acid radical and BOH is an aliphatic or aromatic alcohol.

7. A method according to claim 6 wherein $XO_2/Y_2O_3$ is in the range 20 to 3000.

8. A method according to claim 6 wherein $MOH/XO_2$ is in the range 0.01 to 0.3.

9. A method according to claim 6 wherein $Z^-/Y_2O_3$ is in the range 10 to 100.

10. A method according to claim 6 wherein $Q/Y_2O_3$ is in the range of 1 to 500.

11. A method according to claim 6 wherein $H_2O/XO_2$ is in the range 15 to 300.

12. A method according to claim 6 wherein $BOH/Y_2O_3$ is in the range 0 to 1000.

13. A method according to any one of claims 5, 6 or 7 wherein the 4,4'-bipyridyl compound is 4,4'-bipyridyl.

14. A method of making zeolite Nu-6(2) which comprises heating zeolite Nu-6(1) at a temperature in the range 200° to 750° C.

15. A catalyst comprising zeolite Nu-6(2) as claimed in claim 1, claim 2 or claim 3.

16. A method according to claim 6 wherein $XO_2/Y_2O_3$ is in the range 20 to 3000; $MOH/XO_2$ is in the range 0.01 to 0.3; $Z^-/Y_2O_3$ is in the range 10 to 100; $Q/Y_2O_3$ is in the range 1 to 500; $H_2/XO_2$ is in the range 15 to 300; and $BOH/Y_2O_3$ is in the range 0 to 1000.

17. A method according to claim 16 wherein the 4,4'-bipyridyl compound is 4,4'-bipyridyl.

18. A method of making zeolite Nu-6(2) comprising heating zeolite precursor material Nu-6(1) made according to claim 5, 6, 16 or 17 at a temperature in the range of 200° to 750° C.

19. Zeolite precursor material Nu-6(1) having molar compositions expressed by the following formula:
0.5 to 1.5 $R_2O$: $Y_2O_3$: at least 10 $XO_2$: 0 to 2000 $H_2O$
wherein R is a monovalent cation or 1/n of a cation of valency n, X is silicon, and/or germanium, Y is one or more of aluminum, iron, chromium, vanadium, molybdenum, antimony, arsenic, manganese, gallium or boron, and $H_2O$ is water of hydration additional to water notionally present when R is H, and having X-ray diffraction patterns substantially as set out in Table 1.

20. Zeolite precursor material Nu-6(1) according to claim 19 wherein the molar composition is expressed by the formula:
0,5 to 1.5 $R_2O$: $Y_2O_3$: 20 to 1000 $XO_2$: 0 to 2000 $H_2O$.

21. Zeolite precursor material Nu-6(1) according to claim 19 as freshly made having a molar composition expressed by the formula:
0 to 1.8 $M_2O$: 1.0 to 400 Q: $Y_2O_3$: 10 to 5000 $XO_2$: 0 to 2000 $H_2O$
wherein M is an alkali metal, ammonium or hydrogen, Q is a 4,4'-bipyridyl compound and $M_2O+Q$ is equal to or greater than 1.0.

22. A method of making zeolite Nu-6(2) comprising first making the zeolite precursor material Nu-6(1) as defined in claim 19, by reacting an aqueous mixture containing at least one oxide $XO_2$, at least one oxide $Y_2O_3$, and a 4,4'-bipyridyl compound, and thereafter heating the zeolite precursor material Nu-6(1) at a temperature in the range of 200° to 750° C. to form zeolite Nu-6(2).

23. A catalyst comprising zeolite Nu-6(2) as claimed in claim 4.

* * * * *

UNITED STATES PATENT AND TRADEMARK OFFICE
CERTIFICATE OF CORRECTION

PATENT NO. : 4,397,825
DATED : August 9, 1983
INVENTOR(S) : Thomas V. WHITTAM

It is certified that error appears in the above—identified patent and that said Letters Patent is hereby corrected as shown below:

Column 6 line 29 (Example 6) figures "20.6g and 2.47g" should read --206g and 247g-- respectively.

Column 10 line 22 (Example 18) "6Q" should be --2Q--.

Signed and Sealed this

Thirtieth Day of October 1984

[SEAL]

Attest:

GERALD J. MOSSINGHOFF

Attesting Officer

Commissioner of Patents and Trademarks